US00PP14672P29

(12) United States Plant Patent
Hofmann

(10) Patent No.: US PP14,672 P2
(45) Date of Patent: Apr. 6, 2004

(54) NEW GUINEA IMPATIENS PLANT NAMED 'FISNICS SCARLET'

(50) Latin Name: *Impatiens hawkeri*
Varietal Denomination: Fisnics Scarlet

(76) Inventor: Birgit Christa Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/452,981

(22) Filed: Jun. 3, 2003

(51) Int. Cl.[7] ..... A01H 5/00

(52) U.S. Cl. ..... Plt./318

(58) Field of Search ..... Plt./318

*Primary Examiner*—Kent Bell
(74) *Attorney, Agent, or Firm*—C. A. Whealy

(57) ABSTRACT

A new and distinct cultivar of New Guinea Impatiens plant named 'Fisnics Scarlet', characterized by its outwardly spreading and uniformly mounded plant habit; medium growth habit; freely branching and freely flowering habit; medium green-colored foliage; and large, rounded and bright red-colored flowers that are positioned above and beyond the foliage.

1 Drawing Sheet

Botanical classification/cultivar designation: *Impatiens hawkeri* cultivar Fisnics Scarlet.

BACKGROUND OF THE INVENTION

The present Invention relates to a new and distinct cultivar of New Guinea Impatiens plant, botanically known as *Impatiens hawkeri*, and hereinafter referred to by the name 'Fisnics Scarlet'.

The new Impatiens is a product of a planned breeding program conducted by the Inventor in Hillscheid, Germany and Galder, Gran Canaria, Spain. The objective of the breeding program is to develop new medium-sized Impatiens cultivars with an early to medium flowering response and large rounded flowers with attractive coloration.

The new Impatiens originated from a cross-pollination made by the Inventor during the spring of 1999 of the *Impatiens hawkeri* cultivar Danharltorc, disclosed in U.S. Plant Pat. No. 12,092, as the female, or seed, parent with the *Impatiens hawkeri* cultivar Daniboog, not patented, as the male, or pollen, parent. The cultivar Fisnics Scarlet was discovered and selected by the Inventor as a flowering plant within the progeny of the stated cross-pollination in a controlled environment in Galder, Gran Canaria, Spain in April, 2000.

Asexual reproduction of the new cultivar by terminal cuttings taken in Galder, Gran Canaria, Spain, since July, 2000, has shown that the unique features of this new Impatiens are stable and reproduced true to type in successive generations.

SUMMARY OF THE INVENTION

The following traits have been repeatedly observed and are determined to be the unique characteristics of 'Fisnics Scarlet'. These characteristics in combination distinguish 'Fisnics Scarlet' as a new and distinct Impatiens cultivar:

1. Outwardly spreading and uniformly mounded plant habit; medium growth habit.
2. Freely branching and freely flowering habit.
3. Medium green-colored foliage.

4. Large, rounded and bright red-colored flowers that are positioned above and beyond the foliage.

Plants of the new Impatiens can be compared to plants of the female parent, the cultivar Danharltorc. In side-by-side comparisons conducted by the Inventor in Hillscheid, Germany, plants of the new Impatiens differed from plants of the cultivar Danharltorc in the following characteristics:

1. Plants of the new Impatiens were larger than plants of the cultivar Danharltorc.
2. Plants of the new Impatiens and the cultivar Danharltorc differed in leaf venation coloration.
3. Flowers of plants of the new Impatiens were bright red in color whereas flowers of plants of the cultivar Danharltorc were light violet pink in color.

Plants of the new Impatiens can be compared to plants of the male parent, the cultivar Daniboog. In side-by-side comparisons conducted by the Inventor in Hillscheid, Germany, plants of the new Impatiens differed from plants of the cultivar Daniboog in the following characteristics:

1. Plants of the new Impatiens were taller than plants of the cultivar Daniboog.
2. Plants of the new Impatiens were more freely branching than plants of the cultivar Daniboog.
3. Plants of the new Impatiens had slightly smaller and slightly lighter green-colored leaves than plants of the cultivar Daniboog.
4. Flowers of plants of the new Impatiens were larger and flatter than flowers of plants of the cultivar Daniboog.

Plants of the new Impatiens can also be compared to plants of the cultivar Timor, disclosed in U.S. Plant Pat. No. 9,144. In side-by-side comparisons conducted by the Inventor in Hillscheid, Germany, plants of the new Impatiens differed from plants of the cultivar Timor in the following characteristics:

1. Plants of the new Impatiens were larger than plants of the cultivar Timor.
2. Plants of the new Impatiens had broader and slightly lighter green-colored leaves than plants of the cultivar Timor.
3. Plants of the new Impatiens had larger flowers than plants of the cultivar Timor.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisnics Scarlet' grown in a container.

DETAILED BOTANICAL DESCRIPTION

The cultivar Fisnics Scarlet has not been observed under all possible environmental conditions. The phenotype may vary somewhat with variations in environment such as temperature and light intensity, without, however, any variance in genotype.

The aforementioned photograph, following observations and measurements describe plants grown in Hillscheid, Germany, under commercial production practice in a glass-covered greenhouse. Rooted young plants were planted in 12-cm containers in late February and the aforementioned photograph and following observations and measurements were taken about 11 weeks later in early May. During the production of the plants, day temperatures were about 18 to 22° C. and night temperatures were about 16 to 18° C. In the following description, color references are made to The Royal Horticultural Society Colour Chart, 1995 Edition, except where general terms of ordinary dictionary significance are used.

Botanical classification: *Impatiens hawkeri* cultivar Fisnics Scarlet.

Parentage:

*Female parent.*—*Impatiens hawkeri* cultivar Danharltorc, disclosed in U.S. Plant Pat. No. 12,092.

*Male parent.*—*Impatiens hawkeri* cultivar Daniboog, not patented.

Propagation:

*Type cutting.*—Terminal tip cuttings.

*Time to initiate roots.*—Summer: About 8 to 10 days at 24° C. Winter: About 12 to 15 days at 21° C.

*Time to produce a rooted cutting.*—Summer: About 15 days at 24° C. Winter: About 18 to 20 days at 21° C.

*Root description.*—Numerous, fibrous, and freely branching; 158D in color.

Plant description:

*General appearance.*—Outwardly spreading and uniformly mounded plant growth habit; medium growth habit; freely branching habit, dense and bushy appearance; freely flowering. Moderately vigorous.

*Crop time.*—From a rooted cutting, about 9 to 10 weeks are required to produce finished flowering plants in 12-cm containers.

*Plant height.*—About 19.9 cm.

*Plant diameter or spread.*—About 35 to 40 cm.

*Lateral branches.*—Quantity per plant: About 9 to 11. Length: About 15 to 18 cm. Diameter: About 7 to 8 mm. Internode length: About 4.5 to 7.5 cm. Texture: Smooth, glabrous. Color: 144C overlain with 181A.

*Foliage description.*—Arrangement: Primarily in whorls. Length: About 12 to 13 cm. Width: About 4.5 to 5 cm. Shape: Elliptic. Apex: Acuminate. Base: Acute. Margin: Serrulate with ciliation. Texture: Smooth, occasionally slightly rippled longitudinally; glabrous. Color: Developing foliage, upper surface: 137D to 143A. Developing foliage, lower surface: 138B. Fully expanded foliage, upper surface: 137B to 137C. Fully expanded foliage, lower surface: 138B. Venation, upper surface: 48B; lighter than 48B towards the apex. Venation, lower surface: 48B to lighter than 48B. Petiole: Length: About 1 to 1.5 cm. Diameter: About 3 mm. Texture: Smooth, glabrous. Color, upper surface: 51A to 51B. Color, lower surface: 51C.

Flower description:

*Flower type and flowering habit.*—Single, large, rounded, and bright red-colored flowers. Freely and continuously flowering; usually about 8 to 9 flowers and flower buds per lateral branch. Flowers positioned above and beyond the foliage; flowers typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 10 weeks after planting.

*Flower buds.*—Length: About 2.2 cm. Diameter: About 1.4 cm. Shape: Ovoid. Color: 41A.

*Flower length.*—About 7.7 to 8 cm.

*Flower width.*—About 7.5 to 7.6 cm.

*Flower depth.*—About 1 to 1.5 cm.

*Petals.*—Quantity: Five per flower, imbricate. Length: Banner petals: About 3.2 to 3.4 cm. Lateral and base petals: About 3.6 to 3.8 cm. Width: Banner petal: About 5.4 to 5.6 cm. Lateral and base petals: About 3.8 to 5 cm. Shape: Cordate. Apex: Weakly to moderately lobed. Base: Attenuate. Margin: Entire. Aspect: Mostly flat. Texture: Smooth; satiny. Color: When opening, upper surface: 43A. When opening, lower surface: 41A. Fully opened, upper surface: Between 40A and 43A; towards the base, 66D, with development. Fully opened, lower surface: 41A.

*Spur.*—Quantity: One per flower. Length: About 5.5 to 6 cm. Diameter: At apex: About 0.5 mm. At flower: About 2 to 3 mm. Aspect: Curved. Color: Towards apex, 53B; towards base, 53D.

*Peduncles.*—Length: About 5.5 to 6 cm. Diameter: About 2 mm. Texture: Smooth, glabrous. Strength: Strong, flexible. Color: 145B.

*Reproductive organs.*—Androecium: Stamen number: Five fused at anthers, hooded; filaments free. Anther length: About 5 to 6 mm. Anther shape: Obovate. Anther color: 43A; towards the margin, 8D. Pollen amount: Moderate. Pollen color: 8D. Gynoecium: Pistil quantity: One per flower. Pistil length: About 6 to 7 mm. Stigma color: 12D. Style color: 12D. Ovary: Five-celled. Ovary color: Between 141A and 143A.

*Seed/fruit.*—Seed and fruit development has not been observed.

Disease/pest resistance: Plants of the new Impatiens have not been observed to be resistant to pathogens and pests common to Impatiens.

Low temperature tolerance: Plants of the new Impatiens have been observed to tolerate night temperatures of 5° C. with 10° C. day temperatures.

It is claimed:

1. A new and distinct cultivar of New Guinea Impatiens plant named 'Fisnics Scarlet', as illustrated and described.

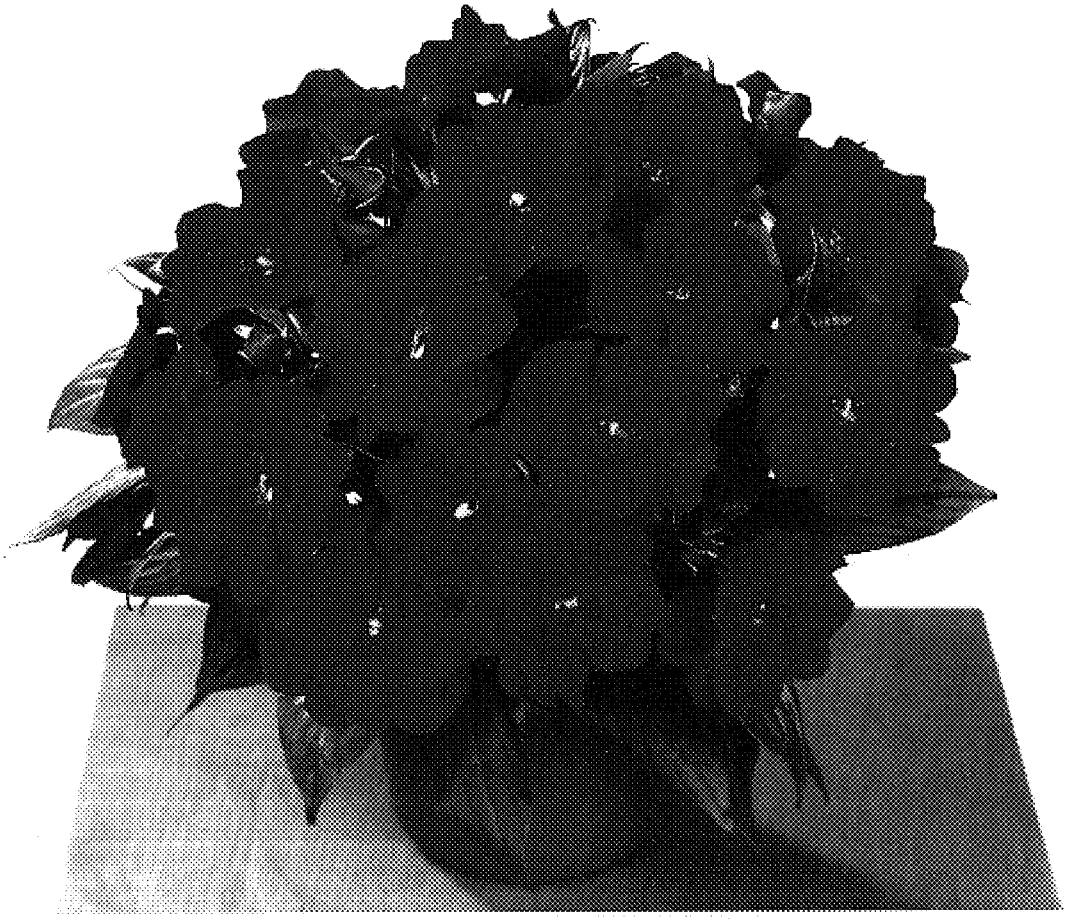

* * * * *